United States Patent [19]
Murray et al.

[11] 3,995,636
[45] Dec. 7, 1976

[54] CONSTRAINED CATAMENIAL DEVICE EMPLOYING ADHESIVE COATING

[76] Inventors: Jerome L. Murray, 652 First Ave., New York, N.Y. 10016; Francis R. Gardiner, 43 Park Road, Sparta, N.J. 07871

[22] Filed: May 7, 1975

[21] Appl. No.: 575,199.

Related U.S. Application Data

[63] Continuation-in-part of Ser. No. 436,391, Jan. 24, 1974.

[52] U.S. Cl. ............................................... 128/285
[51] Int. Cl.² ......................................... A61F 13/20
[58] Field of Search .......... 128/263, 270, 285, 284, 128/296; 19/144.5; 264/321, 360; 260/17.4 ST, 2.5 AK, 2.5 BE

[56] References Cited
UNITED STATES PATENTS

| | | | |
|---|---|---|---|
| 3,306,966 | 2/1967 | Matejcek et al. | 128/285 |
| 3,595,236 | 7/1971 | Corrigan et al. | 128/285 |
| 3,690,321 | 9/1972 | Hirschman | 128/285 |
| 3,900,030 | 5/1975 | Bashan | 128/270 |

Primary Examiner—Robert W. Michell
Assistant Examiner—Henry S. Layton
Attorney, Agent, or Firm—Silverman and Jackson

[57] ABSTRACT

A catamenial device such as a tampon which comprises a segment of a rapidly re-expandable hydrophilic polymeric foam held in compression to less than 50 percent of its original dry volume and a constraining means holding said segment in compression which is adapted to provide lubrication for insertion of said segment into an animal's body cavity and to thereafter rapidly disintegrate, wherein said constraining means comprises a coating material comprising a mixture of sodium bicarbonate and citric acid. Said coating material may be provided by the application of a solution to the surface of said foam segment, or by full impregnation. In a further embodiment, said coating material may be introduced into said foam in particulate form to serve as a novel release agent in a segment which is subsequently constrained within a gelatin capsule.

10 Claims, 3 Drawing Figures

CONSTRAINED CATAMENIAL DEVICE EMPLOYING ADHESIVE COATING

CROSS REFERENCE TO RELATED APPLICATIONS

This application is a Continuation-In-Part of co-pending Ser. No. 436,391 filed on Jan. 24, 1974, by the inventors herein.

BACKGROUND OF THE INVENTION

This invention generally relates to catamenial devices such as tampons and other insertable articles which are prepared from hdrophilic polymeric foam materials.

As noted in the above-identified co-pending application, catamenial devices such as tampns have been prepared from a wide variety of synthetic and naturally occuring organic materials in the form of fibers and sponge-like materials, but have all suffered from various critical defects. Generally, a device such as a tampon which is to be inserted in an easily irritable area of the body cavity must posses a refined texture and flexibility, while, at the same time, possessing a significant absorptive capacity and the ability to rapidly and uniformly re-expand in contact with moisture such as occasioned by the menstrual flow. The latter property is required because the device must assume a reduced size to facilitate its insertion.

Generally, prior art devices have lacked one or more of the above properties, as absorption is usually gained at the expense of size, and flexibility and texture are sacrificed to the ability to undergo re-expansion.

In the context of the above discussion, Applicants sought to provide a device combining all of the favorable characteristics, and, accordingly, developed a catamenial device prepared from a hydrophilic, rapidly re-expandable polymeric foam which is compressed to less than 50 percent of its dry volume and then placed within a soluble, lubricious constraining means such as a capsule. The material most often comprising the capsule of this device is a gelatin compound, which was known to possess the requisite lubricity and solubility as well as non-toxicity to living tissue.

Further experimentation conducted since the development of the above has uncovered a useful alternate material for the preparation of the constraining means which possesses all of the above properties and is easier and less expensive to employ.

SUMMARY OF THE INVENTION

In accordance with the present invention, a catamenial device is disclosed which comprises a hydrophilic, rapidly reexpandable polymeric foam segment which is compressed and placed within a constraining means for an extended period of time, wherein said constraining means comprises a water-soluble coating formed by a composition comprising citric acid and sodium bicarbonate. The coating composition may either be applied topically in solution to the surface of the segment, or the segment may be fully impregnated therewith.

The composition of the present invention may, in an alternate embodiment, be employed as a release agent, by conducting a dry impregnation of the foam prior to shaping and constraint thereof, as disclosed in the co-pending parent application noted above.

Catamenial devices prepared with the coating composition of the invention exhibit favorable storage stability in compression over extended periods of time, and, upon contact with moisture, re-expand rapidly to a volume significantly in excess of original dry volume, due to the effervescence of the composition.

Tampons prepared in accordance herewith likewise unexpectedly perform a mecdicinal function, as the presence of the coating composition in the vaginal canal restores the slightly acidic pH necessary to the prevention of vaginitis during the menstrual period.

Accordingly, it is a principal object of the present invention to provide a catamenial device comprising a hydrophilic polymeric foam held in a compression by a coating composition comprising citric acid and sodium bicarbonate.

It is a further object of the present invention to provide a device as aforesaid which exhibits improved shelf stability under compression, yet is rapidly re-expandable in contact with moisture.

It is yet a further object of the present invention to provide a device as aforesaid which renders medicinal assistance to the vaginal area during the menstrual flow.

It is a still further object of the present invention to provide a method of impregnating a polymeric foam to render said foam more rapidly re-expandable in contact with moisture.

Other objects and advantages will appear from a consideration of the description and accompanying drawings.

DETAILED DESCRIPTION

Figure 1:
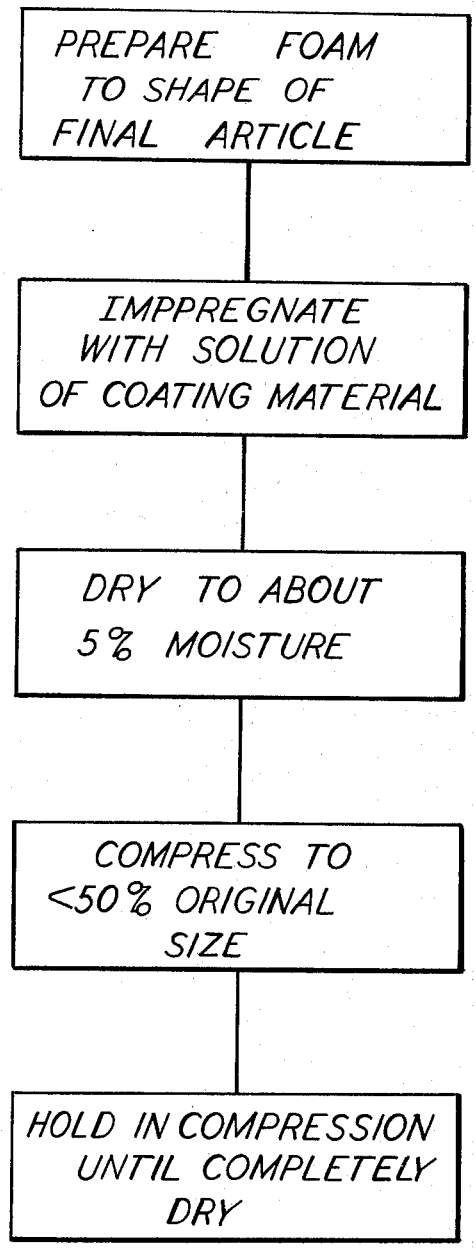
FIG. 1 is a flow diagram outlining the preparation of the device of this invention with a full wet impregnation technique.

In accordance with the present invention, the foregoing objects and advantages are readily obtained.

The present invention comprises a catamenial device such as a tampon which is prepared from a rapidly re-expandable hydrophilic polymeric foam segment which is placed in compression and maintained therein by a constraining means comprising a coating prepared from a composition comprising citric acid and sodium bicarbonate. The composition may be applied in solution as a surface coating, or the foam segment may be impregnated therewith. As a further alternative embodiment, the foam may be dry impregnated with particles of the composition prior to being cut into segments and placed in compression within a constraining means such as a capsule.

The devices and their general preparation, to which the present invention pertains, are disclosed in our copending parent application Ser. No. 436,391, incorporated herein by reference. The foams disclosed therein comprise hydrophilic polyurethane foams or hydrophilic formaldehyde polyvinylalcohol foams. It is preferred, however, that the foam by hydrophilic polyurethane foam. A commercially available hydrophilic polyurethane foam is marketed under the tradename Acquell and is available from the Scott Paper Company. This is a polyurethane foam produced by the reaction of a polyesterdiol and tolylene diisocyanate. The polyesterdiol also contains adipic acid and block copolymers of polyoxyethylene and polyoxypropylene.

Another foam which may be used in accordance with this invention is prepared by, in a first, forming a prepolymer by the reaction of polyethylene glycol and trimethylol propane in a mole ratio of about 2:0.125 to 2:2 respectively, followed by capping the reaction product at all hydroxy locations using tolylene diisocyanate consisting of about an 80/20 mixture of the 2,4 isomer to 2,6 isomer; and in a second step reacting 100 parts by weight of prepolymer with 30 parts by weight of water containing 5 parts by weight of a polyoxyalkylene non-ionic surfactant. A particular non-ionic surfactant which has been found useful is one commercially available under the tradename Pluronic L-64 from the Wyandotte Chemicals Corporation. Although the above comprise the preferred hydrophilic urethane foam materials, other useful hydrophilic urethane foams are produced by varying the above prepolymer to water ratio, as well as varying the water to surfactant ratio. Polymeric foams which are to be employed in the preparation of a tampon assembly should preferably possess a maximum density of about 2.5 lbs./ft.$^3$, as diffuculties arise in the compression and encapsulation of foams whose density exceeds this level.

The general preparation of the constrained device comprises the compression of the foam followed by insertion in the compressed state into a constraining means such as a capsule. Compression of the foam is usually conducted to a reduction of at least about 50% of its original dry volume, and in a preferred embodiment which is useful in tampon manufacture, the foam may be compressed from about less than 25 to about less than 10%. Any conventional type of press or device may be used. This operation may also be in combination with that of placing the compressed foam into the constraining means. The constraining means employed therein comprise a pre-formed capsule structure which, in a preferred embodiment, is prepared from a water-soluble non-toxic material such as gelatin.

The adhesive coating composition comprising the constraining means of the present invention is a mixture of sodium bicarbonate and citric acid employed in roughly equal amounts. It has been discovered that the above mixture serves as a binder when placed on a foam segment and dried, and additionally, when subsequently wetted, provides sufficient effervescence to serve as a blowing agent which enhances the re-expansion of the foam.

Beyond the above advantages, the composition of this invention also possesses a medicinal utility, as it provides a slightly acidic environment which is particularly useful in the vaginal area during the menstrual flow, and prevents the occurrence of vaginitis, which generally resulting from a loss of beneficial bacteria and a change toward an environment of slightly alkaline pH. The restoration of a slightly acidic environment also prevents the undue accumulation of noxious odor and irritation which results from the enzymatic reduction of the uric acid, urea, amino acids and the like constituting the menstrual discharge, to ammonia and volatile amines.

As stated above, the sodium bicarbonate-citric acid composition of the invention may roughly comprise equal amounts of each ingredient. Specifically, the amounts of each may vary within 10%, so that both citric acid and sodium bicarbonate may be present in amounts ranging from 40 to 60% by weight of the total composition. Preparation in the above range has been found to impart the combination of desirable characteristics enumerated earlier.

The composition may be employed in the catamenial device in a number of ways; as a constraining means aplied as a topical liquid coating which dries to form an adhesive outer coat, or by thorough wet impregnation to reside throughout the device. If topical or surface application is employed, the foam segment should first be coated with the composition, after which it may be constrained to the desired volu,e. When the composition is to be employed in liquid form, it should be dispersed in water in a ratio thereto ranging from approximately 1:1 to 5:1 water to composition. When the composition is to be employed strictly as a topical adhesive, the preferred ratio comprises 1:1, as a highly viscous solution results which rapidly fixes the surface of the compressed foam in position. If full impregnation is desired, however, a more dilute solution is preferred to enable the conposition to completely and uniformly penetrate the entire segment.

Referring now to FIG. 1, a flow diagram set out the steps for full wet impregnation of the foam segment. The foam is first prepared to the shape of the final article, which, as illustrated herein, is a tampon. The foam will be cut to dimensions of about 1 × 1 × 2 inches which correspond to the size of a tampon device.

The resulting foam segment is impregnated with a solution of the citric acid-bicarbonate composition, which is preferably employed at a 20 percent concentration. Impregnation may be conducted in a variety of ways. Thus, the solution may be flowed over the foam and allowed to enter by gravity, or an external force such as increased pressure vibration or a partial vacuum may be employed.

After impregnation is complete, the foam is slowly dried to permit roughly 95 percent of the moisture to evaporate from the coating. This can be accomplished at room temperature, or at slightly elevated temperatures.

Once the majority of moisture is removed, the impregnated foam segment is compressed to less than about 50 percent of its original volume. As noted in the above-referenced parent application, compression may be conducted to less than 10% of original volume. Once compressed, the foam may be held at room temperature for a short period of time, or instantaneously constrained by the application of mild heat to harden the coating. The tampon is then complete, and may resemble the illustration of FIG. 3.

In an alternate embodiment of the present invention, the citric acid-sodium bicarbonate composition is dry impregnated into the foam before its preparation into segments for particular end products.

Figure 2:
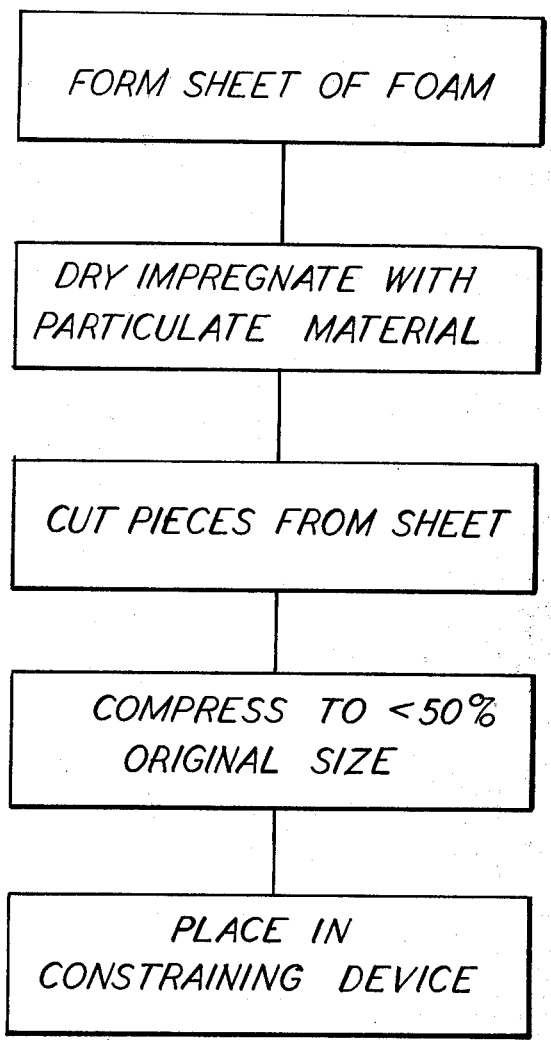
FIG. 2 is a flow diagram outlining the dry impregnation of the foam with the coating composition employed in accordance with the invention.

Referring to FIG. 2, a flow sheet of successive steps for dry impregnation of the foam and the production of articles such as tampons is presented. The hydrophilic foam is formed into a sheet of essentially any reasonable dimensions. For use as a tampon the foam will be formed in a thickness of about 2 inches. The foam sheet is then placed in a chamber and an air stream containing the composition in particulate form is drawn through the foam. The cells of the foam act as a filter and trap most of the solid agent. When the foam contains 10 to 200 percent by weight of the solid agent, it is removed from the air chamber. At this stage, in the manufacture of tampons, the sheet will be cut into individual segments of about 1 inch square. If larger articles are to be manufactured which utilize an entire sheet of foam, or if the foam is initially prepared by a molding process, such as extrusion of a finite length, which yields the ultimately desired shape, this step is eliminated.

After impregnation, and, if necessary, cutting the foam is compressed to less than 50 percent of its original volume. In a preferred embodiment which is useful in tampon manufacture, the foam may be compressed from about less than 25 to about less that 10%. Any conventional type of press or device may be used. This operation may also be in combination with that of placing the compressed foam into the constraining device. As previously discussed, the constraining device which may be employed in this technique, is a gelatin capsule or cylinder. The foam segment, which is prepared for tampon manufacture and measures about 1 × 1 × 2 inches, can be compressed and placed with the capsule in a single step by any of the many known techniques. One useful technique is to have a cylindrical mold of the same interior diameter, which cooperates with a ram which axially thrusts into the mold cavity and forces the foam into the capsule.

The draw string conventionally attached to the tampon may be stitched into place at any time, either to the foam before encapsulation, or to the encapsulated tampon itself. Once placed in the capsule, the foam can be stored indefinitely. As discussed earlier, the gelatin capsule readily dissolves upon contact with moisture, and the foam rapidly expands to contact the vaginal periphery.

The tampons described above may be employed as prepared or may also contain, as desired, various suitable additives such as disinfectants, perfumes, medicaments, deodorants, emollients, pigments and/or dyes. In a further embodiment, the devices of the present invention may be employed to test for the presence of various microorganisms, by the incorporation of suitable chemical indicators. Naturally, the size and shape of the tampons of this invention may vary widely to account for variation in locus of use and function.

Figure 3:
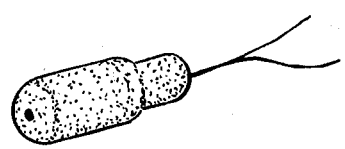
FIG. 3 is a perspective view of a tampon prepared in accordance with the technique of FIG. 1.

Thus, as disclosed in our parent application, the tampon, as illustrated in FIG. 3, may be employed alone for use by digital insertion, or may be mounted upon insertion means usually comprising one or more cylindrical tubes, which serve to position and eject the device within the vaginal canal.

Throughout the specification, all percentages of ingredients are expressed as percent by weight.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:
1. A catamenial device comprising:
   a segment of compressed hydrophilic polymeric foam in compression to less than 50 percent of its original dry volume;
   a constraining means for maintaining said segment in compression, providing lubrication for insertion of said segment into an animal's body cavity, and adapted for rapid disintegration in said body cavity, said constraining means comprising a composition containing citric acid and sodium bicarbonate.
2. The device of claim 1 wherein said compressed hydrophilic foam comprises a polyurethane foam.
3. The device of claim 1 wherein said compression ranges from about les than 25 percent to about less than 10 percent of said original dry volume.
4. The device of clainm 1 further including a withdrawal string affixed to said segment to facilitate removal from said body cavity after use.
5. The device of claim 1 further containing an additive selected from the group consisting of deodorants, disinfectants, perfumes, emollients, medicaments, pigments, dyes and mixtures thereof.
6. The device of claim 1 wherein said segment is topically coated with said constraining means.
7. The deivce of claim 1 wherein said segment is fully impregnated with said constrainig means.
8. A catamenial device comprising:
   a segment of compressed hydrophilic polymeric foam in compression to less than 50 percent of its original dry volume; and
   a constraining means for maintaining said segment in compression, providing lubrication for insertion of said segment into an animal's body cavity, and adapted for rapid disintegration in said body cavity; wherein said segment is impregnated with from 10 to 200 percent by weight of a particulate release agent comprising a composition containing citric acid and sodium bicarbonate.
9. The device of claim 8 wherein said compressed hydrophilic foam comprises a polyurethane foam.
10. The device of claim 8 wherein said compression ranges from about less than 25 percent to about less than 10 percent of said original dry volume.

* * * * *